United States Patent [19]

Wu

[11] 4,412,005
[45] Oct. 25, 1983

[54] DETERMINATION OF TOTAL BILIRUBIN

[75] Inventor: Tai-Wing Wu, Rochester, N.Y.

[73] Assignee: Eastman Kodak Company, Rochester, N.Y.

[21] Appl. No.: 88,230

[22] Filed: Oct. 25, 1979

[51] Int. Cl.³ .............................................. G01N 33/72
[52] U.S. Cl. ....................................... 436/97; 436/170
[58] Field of Search ............................. 23/230 B, 905; 422/55–57; 260/112 R, 112 B; 436/97, 170

[56] References Cited

U.S. PATENT DOCUMENTS 4,069,017 1/1978 Wu et al. ............................ 23/230 B

OTHER PUBLICATIONS

Chiamori et al., *Clin. Chim. Acta.*, vol. 6, pp. 1–6, (1961).
Henry et al., *Clinical Chemistry-Principle and Technics*, 2nd ed., Harper and Row, New York, pp. 1047, 1048, 1070–1073, (1974).
Wu et al., abstract, *Clinical Chemistry*, vol. 25, No. 6, p. 1137, Jun. 1979.
Fog et al., *Scand. J. Clin. Lab. Invest.*, vol. 20, pp. 88–92, (1967).
Hertz et al., *Scand. J. Clin. Lab. Invest.*, vol. 29, pp. 217–230, (1972).

*Primary Examiner*—Arnold Turk
*Attorney, Agent, or Firm*—J. Lanny Tucker

[57] ABSTRACT

A direct, spectrophotometric method for determining the total bilirubin content of an aqueous liquid is provided by detecting the absorption spectrum of the aqueous liquid at a wavelength at which the absorption characteristics of unconjugated bilirubin and conjugated bilirubin are effectively identical. The method is carried out, for example, at a wavelength in the range of from about 385 to 425 nm. An interactive mordant for bilirubin is useful in the assay method to increase assay sensitivity. The assay can be performed as a solution assay or with a "dry chemistry" test element, for example, a multilayer analytical test element.

14 Claims, 18 Drawing Figures

DETERMINATION OF TOTAL BILIRUBIN

FIELD OF THE INVENTION

The present invention relates to a method for determining the total bilirubin content of an aqueous liquid such as a biological fluid, e.g., serum. The assay method of the invention is direct and highly sensitive and may be employed using either "wet chemistry", i.e., analytical chemical techniques sometimes referred to as solution assay techniques wherein chemical reagents are dissolved or suspended in a liquid vehicle; or "dry chemistry", i.e., analytical chemical techniques wherein chemical reagents are incorporated in various substantially "dry-to-the-touch" elements such as monolayer test strips, multilayer analytical test elements and the like.

BACKGROUND OF THE INVENTION

Bilirubin is a degradation product of hemoglobin. It has been estimated that approximately 200–230 mg of bilirubin and its derivatives are formed each day in a normal human adult by the degradation of hemoglobin within the liver, spleen, and bone marrow. Bilirubin has a natural yellow-orange color.

In human body fluids such as bile and serum, bilirubin exists in chiefly two different forms, these forms commonly being referred to in the clinical literature as conjugated bilirubin, $B_c$, and unconjugated bilirubin, $B_u$. Therefore, the total bilirubin content, $B_T$, of any individual body fluid commonly represents the sum of the $B_u$ and $B_c$ components in that fluid.

The diagnostic significance of bilirubin is well established. For example, an excessive amount of bilirubin within the human body, referred to as jaundice, is recognized as evidence of a variety of disease conditions, particularly diseases of the liver.

The literature on various bilirubin assay techniques and methodology is voluminous. Direct, spectrophotometric analysis represents one of the more popular methods for determination of bilirubin owing to its simplicity. Direct, spectrophotometric assays determine the presence and/or concentration of a substance in a liquid by detecting the absorption spectrum of the liquid in a spectral region in which the substance exhibits inherent molar absorptivity.

One particularly useful direct, spectrophotometric assay recently developed for bilirubin is described in Wu et al, U.S. Pat. No. 4,069,017 issued Jan. 17, 1978. This patent describes a colorimetric bilirubin assay using an interactive mordant for bilirubin. The mordanted bilirubin exhibits an enhanced absorption spectrum, thereby increasing bilirubin assay sensitivity and facilitating quantitative "dry chemistry", as well as "wet chemistry", bilirubin assays.

The problem of providing increased assay sensitivity and maintaining relatively low assay error has been a persistent problem associated with direct, spectrophoto-metric bilirubin assays. This problem has become increasingly troublesome as more stringent precision and accuracy demands are imposed, although some progress has been made. For example, hemoglobin spectral interference with bilirubin assays has been identified. Such hemoglobin interference has been reduced by analyzing the absorption spectrum of a liquid sample at several different wavelengths, one or more being specific to hemoglobin, so that bilirubin spectral absorption readings can effectively be corrected for hemoglobin interference. In addition, as noted above, the use of interactive mordants for bilirubin has enhanced the molar absorptivity of bilirubin so that direct, spectrophotometric bilirubin assays can effectively be made on a quantitative basis, even in "dry chemistry" assays which typically require detectable species exhibiting high molar absorptivities.

Notwithstanding the foregoing efforts, the problem of direct, spectrophotometric bilirubin assay error has persisted, particularly for total bilirubin, $B_T$, assays conducted on aqueous samples containing a substantial amount of $B_c$. The present inventor has recently conducted extensive investigation of direct, spectrophoto-metric $B_T$ assays focusing particularly on the individual $B_u$ and $B_c$ components of a $B_T$ assay. This research has identified important $B_c$ and $B_u$ characteristics heretofore unknown or at least unappreciated. For example, although the molecular structure and molecular weight of $B_u$ is well known, the molecular structure and molecular weight of $B_c$, owing to its instability, has only recently been elucidated by the present inventor as set forth in his co-pending patent application Ser. No. 56,584 filed July 11, 1979 and in the paper entitled "Human Conjugated Bilirubin-Isolation, Biosynthesis and Molecular Characterization by Direct, Spectroscopic Analysis", T. W. Wu et al, presented at the American Association for Clinical Chemistry 31st Annual Meeting in New Orleans, La., July 15–20, 1979. An abstract of this paper appears in Clinical Chemistry, Vol. 25, No. 6, page 1137, June, 1979. Thus, the molecular weight of a conjugated form of bilirubin, $B_c$, has been determined to be 918.2 and its molecular structure has been determined to be:

where $R_1$=glucuronic acid and $R_2$=glucuronolactone or $R_1$=glucuronolactone and $R_2$=glucuronic acid In addition, the present inventor has recently developed a new technique for extracting highly purified $B_c$ from body fluids, such as bile and serum, as described in his co-pending patent application U.S. Ser. No. 56,585 filed July 11, 1979.

Based on his study of highly purified $B_c$ and $B_u$, the present inventor has found that $B_u$ and $B_c$ have quite distinct, although overlapping, absorption spectra. For example, although both $B_c$ and $B_u$ absorb in the 435 to 460 nm region of the spectrum, their individual absorption characteristics in this spectral region are quite different. This is highly significant because direct, spectrophotometric assays of $B_T$ are made in the 435–460 nm region of the spectrum using calibrators having a bilirubin content comprised solely of $B_u$. This is based on the assumption that $B_c$ has an absorption spectrum identical to that of $B_u$ as reported by Henry et al, Clinical Chemistry, Principles And Technics, Harper and Row, p. 1071 (1974). Significant assay errors therefore occur when direct, spectrophotometric $B_T$ assays are carried out in the 435–460 nm spectral region on any aqueous sample having a substantial $B_c$ concentration.

The elimination or at least substantial reduction of the foregoing assay error problem associated with direct, spectrophotometric assays of $B_T$ would permit use of this otherwise highly effective, straightforward approach to $B_T$ assays and would therefore represent a highly useful contribution to the art.

SUMMARY OF THE INVENTION

The present invention features a spectrophotometric method for the determination of the total bilirubin ($B_T$) content of an aqueous liquid. The method comprises detecting the absorption spectrum of the aqueous liquid at a wavelength at which the absorption characteristics of unconjugated bilirubin, $B_u$, are effectively identical to those of conjugated bilirubin, $B_c$.

The present invention significantly reduces assay error arising from the dissimilar absorption characteristics of $B_u$ and $B_c$ in the wavelength range in which direct, spectrophotometric assays for total bilirubin have previously been conducted, that is, within the wavelength range of from about 435 to 460 nm. This highly advantageous reduction in assay error results from the unexpected discovery that the absorption characteristics of $B_u$ and $B_c$ are effectively identical at certain wavelengths outside the 435–460 nm range. The present method for the determination of total bilirubin preferably detects the absorption spectrum of the aqueous liquid under analysis at a wavelength within the range of from about 385 to 425 nm, most preferably in the range of from about 395 to 420 nm.

In accord with certain preferred embodiments of the invention, the aqueous liquid under analysis for its total bilirubin content and an interactive mordant composition for bilirubin are contacted together to mordant bilirubin. Mordanted bilirubin, including both mordanted $B_c$ and mordanted $B_u$, exhibits enhanced absorption in the visible spectral range used for detection of total bilirubin in accord with the present invention, thereby providing increased assay sensitivity.

The method of the invention is conveniently carried out using either "wet chemistry" or "dry chemistry" analytical techniques. In a preferred embodiment, the analysis method of the invention is carried out with a dry chemistry analytical element as follows:

(a) contacting together an aqueous liquid to be analyzed for $B_T$ and an analytical element having an essentially dry reagent zone comprising an interactive mordant, as described above, to mordant bilirubin, and (b) spectrophotometrically detecting the absorption spectrum of the aqueous liquid at a wavelength at which the absorption characteristics of mordanted $B_u$ and mordanted $B_c$ are effectively identical.

Preferably, step (b) above is carried out in the spectral region of from about 385–425 nm, most preferably 395–420 nm.

A preferred dry chemistry analytical element employed in the method of the invention is a multi-zone element comprising a reagent zone as described above and a spreading zone which can effectively distribute and meter the aqueous liquid under analysis to the reagent zone. For many applications, multi-zone elements are preferably integral elements wherein the spreading zone and reagent zone are superposed layers in fluid contact with one another under conditions of use of the element. Optionally, these layers are carried on a support, such as a "radiation-transmissive" support. In certain preferred aspects of this embodiment, an additional "radiation-blocking" zone is sandwiched between the spreading zone and reagent zone of a multi-zone element of the invention to promote additional assay precision, as illustrated in certain of the appended Examples.

The terms "reagent-transmissive" and "radiation-blocking" refer to zones, supports, and other layers of an element that transmit or block, respectively, effective passage of electromagnetic radiation used to detect an analytical result produced in an element in accord with the invention. Typically, such "radiation-transmissive" or "radiation-blocking" zones, supports, and other layers, transmit or block, respectively, radiation having a wave-length within the range of from about 200 to 900 nm.

DESCRIPTION OF THE PREFERRED EMBODIMENTS

The phrase "absorption characteristics" refers herein to the optical characteristics of a substance as determined at a given wavelength of detecting radiation. Absorption characteristics can be quantitatively expressed by various absorption measurements including, for example, absorbance (A), transmission density ($D_T$), reflection density ($D_R$), and the like. The particular spectrophotometric measurement selected in any given assay will vary depending, for example, upon the type of assay conducted. Thus, in "wet chemistry" or solution assays, the absorption characteristics of a substance in an aqueous liquid are conveniently measured by spectrophotometrically detecting the absorbance of the aqueous liquid containing the substance. In "dry chemistry" assays, the absorption characteristics of a substance in an aqueous liquid are conveniently measured by contacting together a sample of the liquid under analysis and a test element, and spectrophotometrically detecting the $D_T$ or $D_R$ produced in the element by the liquid, the choice of $D_T$ or $D_R$ measurement depending upon whether the test element transmits or reflects the detecting radiation.

As stated above, the present method is carried out at a wavelength at which the absorption characteristics of $B_u$ and $B_c$ are effectively identical. This means, at this wavelength, the absorption characteristics of $B_u$ and $B_c$ are spectrophotometrically matched such that a calibrator composed of $B_u$, $B_c$, or a mixture of $B_u$ and $B_c$ will provide an accurate assay of the total bilirubin content of an aqueous liquid containing both $B_c$ and $B_u$. Accordingly, making a single, direct, spectrophotometric measurement on an aqueous liquid containing both $B_u$ and $B_c$ at this wavelength provides an accurate assay for $B_T$.

The term "accurate assay" means that the present $B_T$ analysis method, when used, for example, to analyze the $B_T$ content of serum samples containing both $B_u$ and $B_c$, correlates with a commonly accepted reference assay, such as the Jendrassik-Grof method, having a correlation coefficient (r) of greater than 0.98, a slope of regression analysis of 1.0±0.1, and an intercept of the regression analysis (Sy.x) equal to 0.0±0.5. The Jendrassik-Grof reference method noted above is described in Fundamentals of Clinical Chemistry, N.W. Tietz, Ed., 2nd Edition, W. B. Saunders Co., Philadelphia, Pa. (1964), pages 1037–1040. Further details relative to the accuracy of the present method are set forth in appended Examples 6 and 7.

The theoretical basis of this invention resides in the discovery that the absorption spectra of $B_c$ and $B_u$ are different, but that a wavelength exists at which the molar absorption coefficients of $B_u$ and $B_c$ are effectively identical. Thus, applying Beer's Law, the molar concentration of $B_T$ in an aqueous liquid containing $B_u$ and $B_c$ is obtained according to the present spectrophotometric method on the basis that, at this wavelength, the molar concentration of $B_T$ is directly proportional to the total detected absorbance or transmission density of the aqueous liquid. That is, at this wavelength the total detected absorbance or transmission density of the aqueous liquid represents the sum of the absorbance or transmission density of $B_u$ and the absorbance or transmission density of $B_c$. Although Beer's Law does not directly apply to reflection density, various transforms are available which permit, for example, the conversion of measured reflection densities to transmission densities. One such transform is illustrated hereinafter in Example 8. Accordingly, the specific spectrophotometric measurement made in the present $B_T$ assay is not critical, and depending upon the type of assay, can be any one of the above-noted measurements including absorbance, transmission density, or reflection density.

To further illustrate the invention, reference is made to attached FIGS. 1a–1i. FIGS. 1a–1i illustrate the change in the absorbance of two series of aqueous solutions, one series containing essentially pure $B_c$ and the other containing essentially pure $B_u$, versus the change in concentration of $B_c$ or $B_u$ over the range of 0 to 2 mg/dl. Each of FIGS. 1a–1i is at a different wavelength. (The "normal" range of total bilirubin concentration in adult serum is generally regarded as about 0.9 to 1.1 mg/dl.) As shown in FIGS. 1a–1i, the absorbance of identical quantities of $B_u$ and $B_c$ become effectively identical over the wavelength range of from about 395 to 425 nm, particularly 400 to 420 nm, whereas a substantial difference in absorbance is exhibited by identical quantities of $B_c$ and $B_u$ at wavelengths above and below these values. In particular, a significant difference in absorbance is evident over the wavelength range of 435 to 460 nm which corresponds to the wavelength range at which direct, spectophotometric $B_T$ assays have previously been performed. Thus, if a direct, spectrophotometric $B_T$ assay is conducted at a wavelength in the range of from about 435 to 460 nm on a liquid sample containing significant quantities of both $B_c$ and $B_u$ using a calibrator having a bilirubin content comprised solely of $B_u$, the resultant absorbance detected cannot be accurately correlated to $B_T$.

Figure 1A:
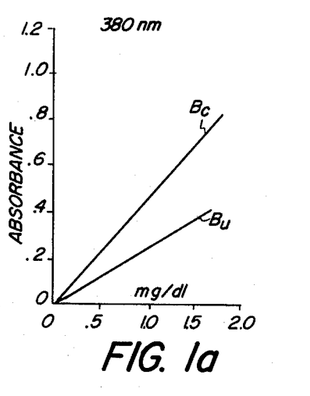
FIGS. 1a–1i, 2–5, 6a–6c, and 7a–7b are graphs illustrating the absorption characteristics of $B_c$ and $B_u$ at various wavelengths.
Figure 1B:
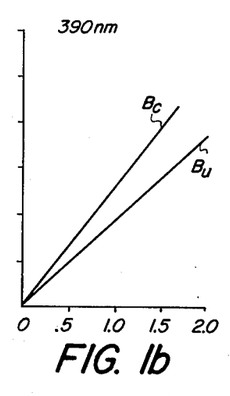
Figure 1C:
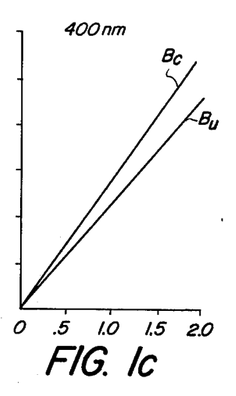
Figure 1D:
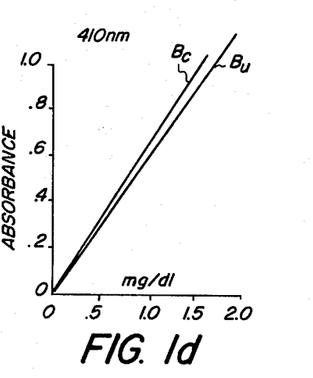
Figure 1E:
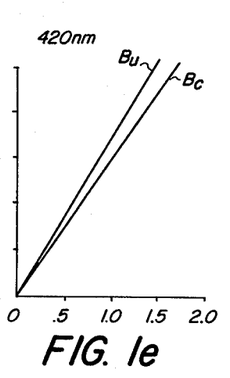
Figure 1F:
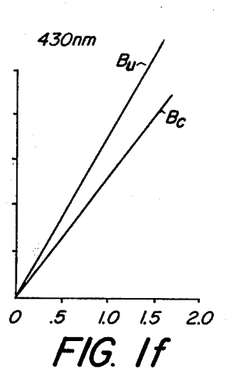
Figure 1G:
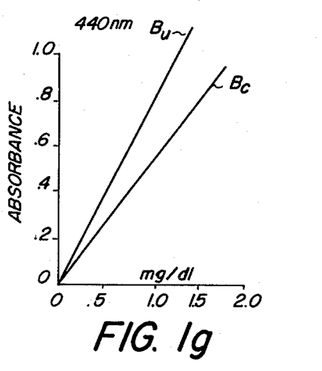
Figure 1H:
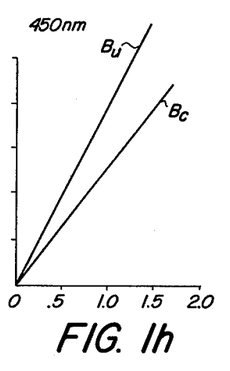
Figure 1I:
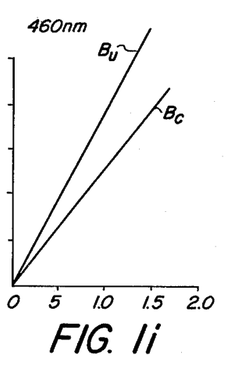
Figure 2:
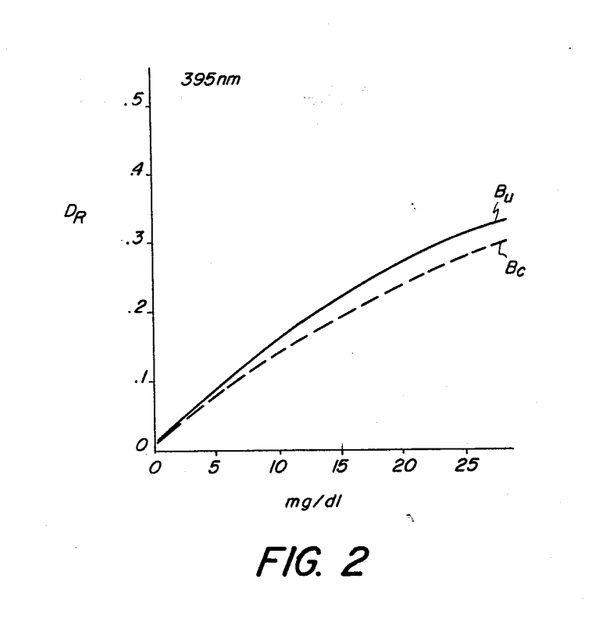
Figure 3:
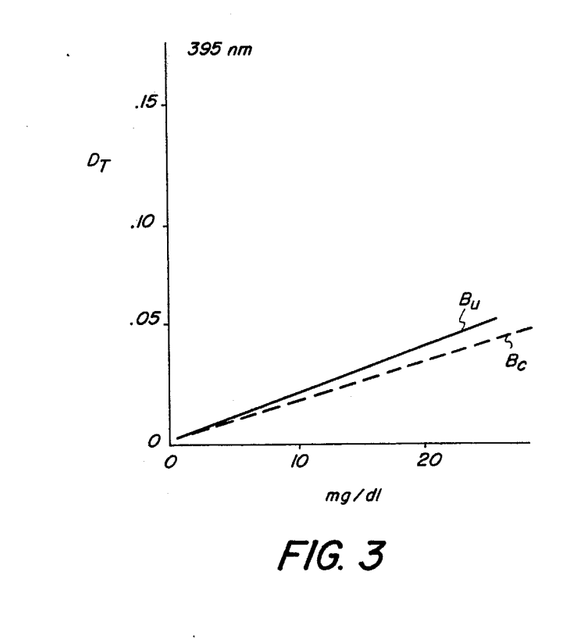
Figure 4:
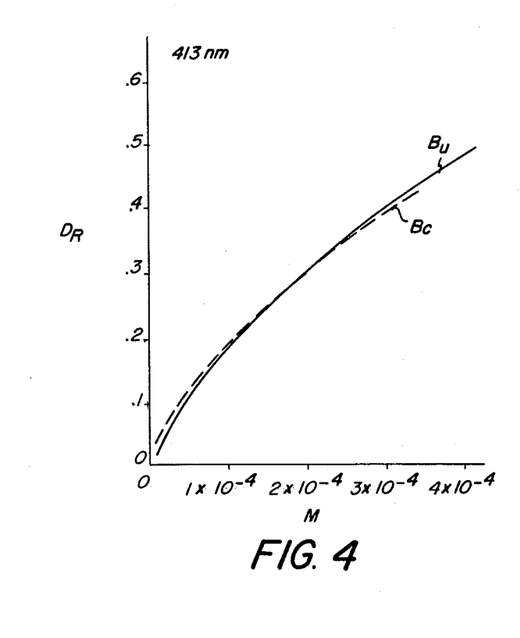
Figure 5:
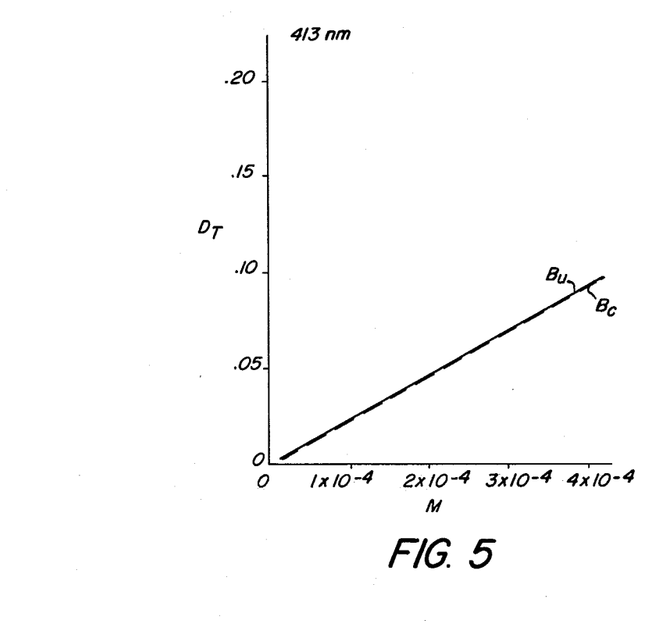

The data in FIGS. 1a–1i express $B_u$ and $B_c$ concentrations in mg/dl. Because $B_u$ and $B_c$ have differing molecular weights (M.W.), $B_u$ having a M.W. of about 584 and $B_c$ having a M.W. of about 918, the optimum wavelength selected for the total bilirubin assay method of the invention will vary somewhat depending upon whether the concentration units of the assay are expressed in mg/dl or molarity (moles/l). This is illustrated, for example, in FIGS. 2–5 which are based on the work described in greater detail in appended Example 8. Under the specific assay conditions used in Example 8, FIGS. 2 and 3 illustrate that good agreement was found between the absorption characteristics of equal concentrations of $B_u$ and $B_c$, when expressed in mg/dl, at a wavelength of 395 nm. Under the same assay conditions, FIGS. 4 and 5 illustrate that good agreement was found between the absorption characteristics of equal concentrations of $B_u$ and $B_c$, when expressed in moles/l, at a wavelength of 413 nm.

The pH and temperature conditions under which the present assay method is carried out are variable. In certain preferred embodiments, the assay is carried out at a pH range of from about 6.5 to about 10.0, preferably about 6.8 to about 8.2, and at a temperature within the range of from about 15° to about 60° C., preferably from about 20° to about 50° C. In those embodiments of the assay which employ an interactive mordant one can vary the aforementioned pH and temperature to values above or below the stated ranges depending upon the particular mordant selected, providing, of course, that one does not use a pH or temperature which causes undesired side reactions or significant degradation of bilirubin.

To aid in maintaining the pH within the preferred range of from about 6.5 to about 10.0, the bilirubin determination is typically carried out in the presence of buffer. Various buffers are useful. A partial listing of representative buffers is described by Good in Biochemistry, 5, 467 (1966). Particularly good results have been obtained using N,N-bis(2-hydroxyethyl)glycine, in an amount effective to maintain the pH of the aqueous test sample in the presence of the interactive mordant within the range of from about 6.8 to about 8.2, preferably 7 to 8.0.

In the conduct of the total bilirubin assay of the invention, bilirubin "effectors" or "promoters", as they are sometimes called, are added, if desired. These effectors are employed with or without the use of the interactive mordants present in certain preferred embodiments of the present invention. Such "effectors" or "promoters" are known for use in bilirubin assays as noted by Henry et al in Clinical Chemistry, Principles and Technics, pages 1047 and 1048, referred to in the "Background of the Invention" of this specification. A partial listing of representative effectors includes caffeine, sodium benzoate, gum arabic, salicylate, and bile salts. The precise mechanism of these effectors is not fully understood although they may serve as solubilizing agents for the various bilirubin components. In any case, a combination of caffeine and sodium benzoate has been found especially useful in the present invention.

Figure 6A:
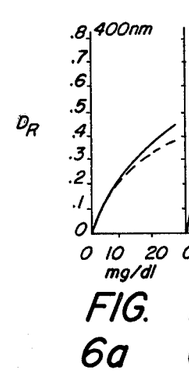
Figure 7A:
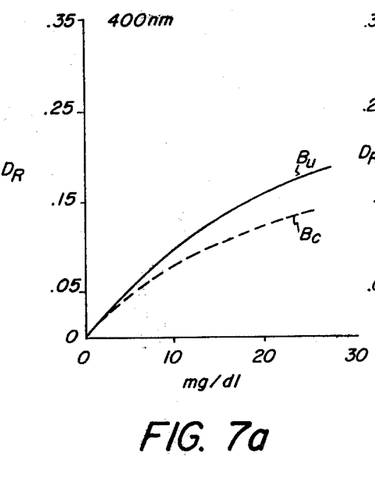

In a preferred embodiment of the present method, the aqueous liquid is contacted under the aforementioned pH and temperature conditions with an interactive mordant to mordant the $B_c$ and $B_u$ contained therein, and the absorption spectrum of the liquid is detected at a wavelength at which these two different mordanted bilirubin components exhibit effectively identical absorption characteristics. The spectrum detected at this wavelength represents both the individual mordanted $B_u$ and mordanted $B_c$ spectra. In this embodiment, the molar absorptivity of both mordanted $B_u$ and mordanted $B_c$ is significantly enhanced over that of unmordanted $B_u$ and $B_c$, thereby facilitating the detection of total bilirubin. To demonstrate this, the absorption spectra of mordanted $B_c$ and $B_u$ at 400 nm as shown in FIG. 6a are compared to those of unmordanted $B_c$ and $B_u$ at the same wavelength as shown in FIG. 7a.

The detection of the absorption characteristics of total bilirubin is carried out in the present assay by any of a variety of well-known absorption detection devices and techniques. Typically, such detection is carried out at a predetermined time, following the contacting together of the aqueous sample and interactive mordant, if one is used. Accordingly, the resultant spectral data is readily correlated to, for example, a calibration curve based on the spectral data obtained from a series of aqueous liquid controls containing known amounts of $B_u$, $B_c$, or mixtures of $B_u$ and $B_C$ as determined at the same or a related predetermined time interval.

The interactive mordants employed in certain preferred embodiments of the present assay method correspond to the mordants for bilirubin described in the aforementioned U.S. Pat. No. 4,069,017. In general, these mordants have multiple binding sites for bilirubin and comprise at least one moiety having a hydrophobic organic matrix and a charg-bearing cationic group. Such mordants can be monomeric or polymeric, with especially preferred embodiments of such mordants represented by homopolymers or copolymers containing repeating units having the above-defined properties. Materials having these properties and compositions bind both $B_c$ and $B_u$ and therefore these materials function as mordants for the total bilirubin content of an aqueous liquid. Bilirubin components, i.e., $B_c$ and $B_u$, mordanted by the binding sites of such interactive mordants exhibit a significant enhancement in molar absorptivity as compared to the unmordanted components, as illustrated hereinabove, thereby advantageously increasing the sensitivity of the present assay method. The charge-bearing cationic group present in the mordant typically retains its cationic charge in an aqueous environment regardless of pH fluctuations in the environment. The charge properties of the cationic group in the interactive mordant are therefore insensitive to variations in pH.

Especially preferred polymeric interactive mordants have in their polymer chain monomeric units of Formula I below:

I.

wherein

A represents an organo group and constitutes a portion of a polymer backbone;

Q represents a chemical bond(s) or a chemical group linking $M^\oplus$ to A;

$M^\oplus$ represents a hydrophobic organic moiety containing a cation, preferably a quaternary ammonium or phosphonium group; and $X^\oplus$ represents an acid anion such as a halide ion, for example, chloride or bromide; nitrate; methosulfate; p-toluenesulfonate; or an equivalent anion.

In certain especially useful embodiments, $M^\oplus$ represents a quaternary ammonium or phosphonium group having Formulas II or III below:

II.

III.

wherein each of $R^1$, $R^2$, and $R^3$, which are the same or different, represent an aryl, an aralkyl, or an alkaryl group having from about 5 to 20 carbon atoms or an alkyl group having from 1 to about 10 carbon atoms, preferably 4 to about 10 carbon atoms.

Preferably, Q, in Formula I represents a hydrocarbon group, preferably an arylene, arylenealkylene, alkylenearylene, arylenebisalkylene, or alkylenebisarylene group. Generally, although not required, Q contains from about 5 to 10 carbon atoms.

As will be appreciated, A in Formula I above is variable depending upon the particular polymeric backbone selected for use. Especially good results, however, have been obtained when A represents an alkylene group. Typically, such alkylene groups contain from about 2 to 10 carbon atoms.

Copolymers particularly useful as interactive mordants include copolymers containing about 10 to 90 wt percent of repeating units having Formula I hereinabove, and up to about 90 weight percent of additional repeating units comprising the residue of non-interfering monomers. The term "non-interfering repeating units (or monomers)" is used herein to include chemical materials which do not chemically or physically interfere with the above-described mordanting of bilirubin. Monomer precursors which provide such non-interfering repeating units and which also impart hydrophobicity to the resultant mordant copolymer include addition-polymerizable aliphatic and aromatic hydrocarbons, such as olefins, substituted olefins, styrene, and substituted styrenes; alkylacrylates and methacrylates and derivatives thereof; and known equivalents for such monomer precursors. In addition, if desired, difunctional crosslinking groups introduced into such copolymers will provide crosslinked copolymers useful as interactive mordants within the scope of the present invention.

A partial listing of individual representative interactive mordants useful in the method of the invention includes the following materials:

TABLE I

| Name | Structure |
|---|---|
| 1. Poly(N,N,N—trimethyl-N—vinyl-benzylammonium chloride) | $\left[-CH_2-CH-\underset{\underset{\underset{CH_3}{|}}{\overset{\overset{CH_2}{|}}{CH_3-N^{\oplus}-CH_3}}}{C_6H_4}-\right]\ Cl^{\ominus}$ |
| 2. Poly[styrene-co-benzyl-(dimethyl)-p-vinyl-benzyl-ammonium chloride] | $\left[-CH_2-CH(C_6H_5)-\right]\left[-CH_2CH-C_6H_4-CH_2-\overset{\overset{CH_3}{|}}{\underset{\underset{CH_2-C_6H_5}{|}}{N^{\oplus}}}-CH_3\right]\ Cl^{\ominus}$ |
| 3. Poly(N,N,N—trioctyl-N—vinyl-benzylphosphonium chloride) | $\left[-CH_2-CH-C_6H_4-CH_2-\underset{\underset{C_8H_{17}}{|}}{\overset{\overset{C_8H_{17}}{|}}{P^{\oplus}}}-C_8H_{17}\right]\ Cl^{\ominus}$ |
| 4. Poly[styrene-co-(vinylbenzyl)-(trihexyl)-ammonium chloride] | $\left[-CH_2-CH(C_6H_5)-\right]\left[-CH_2-CH-C_6H_4-CH_2-\underset{\underset{C_6H_{13}}{|}}{\overset{\overset{C_6H_{13}}{|}}{N^{\oplus}}}-C_6H_{13}\right]\ Cl^{\ominus}$ |

TABLE I-continued

| Name | Structure |
|---|---|
| 5. Poly(N,N,N—trimethyl-N—vinylbenzylammonium chloride-co-styrene) |  |
| 6. Poly(styrene-co-N—vinyl-benzyl-N—benzyl-N,N—dimethyl-ammonium chloride-co-divinyl-benzene) |  |

Further extended description of such interactive mordants including methods of preparing such compositions will be found in U.S. Pat. No. 4,069,017 hereby incorporated by reference.

The amount of the above-described interactive mordants for bilirubin which is used in the present method for total bilirubin analysis can vary. Typically, in any given case, the amount of such interactive mordant will depend upon the particular range of bilirubin content, i.e., the "dynamic range", over which a specific bilirubin assay is designed to be useful. In accord with various preferred embodiments wherein 1 mole of bilirubin is bound or mordanted to an interactive mordant containing 1 molar equivalent amount of binding site for bilirubin, there should be sufficient interactive mordant to provide at least one molar equivalent of binding site for the maximum moles of bilirubin for which that assay is intended.

The amount of the interactive, polymeric mordant required will depend upon the average number of binding sites for bilirubin in the polymer and, as noted above, the dynamic range over which a specific bilirubin assay which employs such polymeric mordant is designed to be useful. In a preferred embodiment wherein a polymeric mordant, such as any one of polymeric mordants 2 and 4–6 listed above, is employed and wherein such polymeric mordant is prepared from an intermediate copolymer of styrene and vinylbenzyl chloride having an inherent viscosity (as measured at 25° C. in benzene at a concentration of 0.25 g/dl) of about 0.15 to 1.0, one typically employs an amount of polymeric mordant within the range of from about 0.01 to about 1.0 g/dl of mordant to provide an assay having a dynamic range of about 0.1 to 50 mg/dl of total bilirubin.

In general, an excess amount of interactive mordant is useful in the present total bilirubin analysis method so that one can accelerate the interaction of bilirubin with the mordant to obtain the desired enhancement in spectral properties of the mordanted bilirubin.

Wet-Chemistry Assay

When the present total bilirubin analysis method is carried out as a wet chemistry or solution assay, analysis is conveniently performed by introduction of the aqueous liquid to be assayed into a suitable "wet" reaction zone, such as a radiation-transmissive container. In those embodiments which employ a mordant, an appropriate interactive mordant is also introduced into the reaction zone to contact the aqueous liquid to be assayed. The mordant is added directly as a dry powder or in the form of a solution or dispersion containing the desired mordant admixed in a non-interfering liquid medium. Such non-interfering liquids include those liquids which, under conditions of use, do not substantially interfere with the interaction of bilirubin and mordant or provide unwanted adsorption or emission at the characteristic absorption wavelengths used in the present assay method. Such non-interfering liquids include a variety of both aqueous and organic liquids. Typically, because of the application of the method to the analysis of biological fluids, the use of an aqueous liquid as the non-interfering liquid is preferred. If desired, and in a preferred embodiment, one or more buffers as described hereinabove is also introduced into the reaction zone to facilitate the performance of the assay in the preferred pH range of from about 6.5 to about 10.0.

When the analysis method is carried out as a "wet" assay for bilirubin, a preliminary step of treating the bilirubin-containing liquid test sample to dissociate the bilirubin from various materials to which it may be bound is quite desirable. For example, where the liquid test sample is serum, a large amount of the bilirubin is bound to serum protein, primarily albumin. Various techniques have been devised in the art and are well known to dissociate bilirubin from materials such as albumin. These methods include the use of various protein precipitation techniques, sample dilution techniques, and the like. A review of many of these different procedures is found, for example, in the aforementioned Henry et al publication, i.e., Clinical Chemistry, Principles and Technics, 2nd Edition (1974), pages 1042–1079.

Following any optional preliminary treatment of the bilirubin-containing test sample as described above and contacting together the test sample with any optional components such as a mordant and buffer, the assay is carried out, preferably in the dark or under yellow safelight conditions, to avoid light induced degradation of bilirubin. In those embodiments which employ an interactive mordant, the assay mixture containing the test sample and mordant is incubated for a period effective to interact the bilirubin with the test sample and the interactive mordant. Thereafter, or during this step, the wet reaction zone containing the assay mixture is subjected to spectrophotometric detection as described hereinabove.

Where an incubation period is employed, the time is typically quite short, on the order of seconds or minutes, typically within the range of from about 1 second to about 10 minutes, preferably 30 seconds to about 7 minutes. If desired, stirring or mixing of the assay mixture is carried out during the incubation period to facilitate interaction of the bilirubin and interactive mordant, if one is employed. The temperature range maintained during the assay, as well as the subsequent detection steps, is as stated hereinabove.

Dry-Chemistry Assay

Because of handling ease and overall convenience features as well as the capability of providing quantitative analytical results, total bilirubin analysis in accord with the present invention by use of a "dry chemistry" analytical element is especially preferred. Such an element comprises an essentially dry (i.e., dry-to-the-touch) reagent zone permeable to bilirubin and containing the above-described interactive mordant, if one is employed. An essentially dry spreading zone and/or additional zones can also be present in the analytical elements. A preferred analytical element comprises at least two distinct zones which are in "fluid contact" with one another under conditions of use. Fluid contact has reference to the ability of a liquid to pass between distinct zones of an element, even though the zones may be separated by intervening zones or initially spaced apart. Other zones which are present in the element, if desired, include radiation-blocking zones, subbing zones, and the like.

Further description of specific radiation-blocking zones, subbing zones, and certain other optional zones or layers is found in the following description of a preferred embodiment of a multi-zone element.

Preferably, although not necessarily, the various zones are present in an element as superposed, contiguous layers. Typically these layers are carried on a support, preferably a radiation transmissive support. Although preferred analytical elements of the invention are composed of superposed, contiguous layers, other elements can be prepared and employed in the method of the invention having different structural arrangements such as the use of an element having two adjacent abutting zones, namely a spreading zone and a reagent zone, both carried on a support, if necessary or desired. Such an element is illustrated, for example, in FIG. 2 of the aforementioned U.S. Pat. No. 4,069,017. For purposes of convenience and for illustrating the best mode of the invention, the dry chemistry elements employed in the invention will hereinafter be described in terms of their structure and characteristics as observed in a multilayer, integral analytical element wherein the different zones are present as superposed, contiguous layers carried on a radiation-transmissive support.

In one preferred embodiment, an integral analytical element of this invention comprises a radiation-transmissive support having thereon, (1) a reagent layer that is permeable to at least bilirubin and which optionally contains an interactive mordant for bilirubin as described above, and (2) a reflecting-spreading layer that is permeable to bilirubin. The reagent layer is interposed between the support and the reflecting-spreading layer. Also, the reflecting-spreading layer is preferably of substantially uniform permeability to bilirubin. Preferably, the reagent layer is substantially impermeable to protein materials having a molecular weight substantially greater than that of bilirubin, e.g., albumin and other proteins having a molecular weight in the region of 60,000 (dalton units) or higher. If desired, an optional radiation-blocking layer is interposed between the reagent layer and reflecting-spreading layer to reduce optical interference from other serum components such as hemoglobin and derivatives thereof.

In accordance with a further aspect of the foregoing preferred embodiment, the spreading layer is a non-fibrous, spreading layer, desirably isotropically porous. More preferably, all layers in the element are non-fibrous, to enhance quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading or with detection of the analytical result by radiometric means.

Useful spreading layers are prepared using a variety of both fibrous and non-fibrous components. Especially preferred spreading layers containing non-fibrous components are more fully described in U.S. Pat. No. 3,992,158, issued Nov. 16, 1976. In one aspect such non-fibrous spreading layers are prepared from particulate materials, all desirably chemically inert to sample components under analysis. Particulate materials such as pigments, diatomaceous earth, microcrystalline colloidal materials derived from natural or synthetic polymers, e.g., microcrystalline cellulose, glass or resinous beads, and the like, can advantageously be employed in such particulate spreading layers as described in U.S. Pat. No. 3,992,158. As an alternative or an addition to such particulate materials, these preferred non-fibrous spreading layer compositions are prepared using porous polymer compositions such as "blush" polymer compositions, as also described in detail in U.S. Pat. No. 3,992,158.

The thickness of the spreading layer is variable and will depend in part on the intended sample volume, which for convenience and cleanliness the spreading layer should be able to absorb completely, and on the void volume of the layer, which also affects the amount of sample that can be absorbed into the layer. Spreading layers of from about 60 microns to about 300 microns dry thickness have been found particularly useful. However, wider variations and thicknesses are acceptable and may be desirable for particular elements.

Reagent layers employed in the dry chemistry elements of the invention include a matrix permeable to bilirubin in which the interactive, mordant, if one is used, is distributed, i.e., dissolved or dispersed. However, because many of the interactive mordants are polymeric and may themselves be film-forming or otherwise readily coatable as a uniform layer or zone, a separate matrix material is not always required when a mordant is employed. The choice of a matrix material is, of course, variable and dependent on the components such as optional mordant and buffer distributed therein. In any case, the matrix material should be "non-interfering" with respect to any mordant contained therein, i.e., the matrix material should be incapable of itself binding or mordanting to the interactive mordant. Further detail regarding reagent layers useful herein may be found by reference to U.S. Pat. No. 4,069,017.

As is the case for the "wet chemistry" assay described herein, a "dry chemistry" analytical element of the invention preferably contains an appropriate buffer. The buffer is incorporated in the reagent layer or in one or more of the other layers present in a particular analytical element of the invention in an amount sufficient to impart to the reagent layer, under conditions of use of the element, a pH within the range noted hereinabove.

In preparing integral analytical elements of this invention, the layers can be preformed as separate layers which are laminated together prior to use or maintained as separate layers until brought into fluid contact when the element is in use. Detailed description of techniques for the preparation and manufacture of these dry chemistry test elements as described herein is found by reference to U.S. Pat. Nos. 3,992,158 and 4,069,017 noted above.

As mentioned previously herein, the present analytical elements are self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 200 nm and about 900 nm.

In one or more layers of the element, it is advantageous to incorporate surfactant materials such as anionic and nonionic surfactant materials. The surfactant(s) enhances coatability of layer formulations and enhances the extent and rate of spreading in spreading layers that are not easily wetted by liquid samples in the absence of an aid such as a surfactant. In particular, it is desirable to incorporate a relatively large amount of a surfactant, such as a nonionic surfactant, in the spreading layer of the elements of the invention to normalize transport of bilirubin contained in an aqueous proteinaceous liquid sample in and through this layer of the element. Such normalization refers to obtaining within the spreading layer an equivalent penetration of the solvent medium and brilirubin contained in various applied samples of aqueous proteinaceous liquids, notwithstanding variations in protein concentration between such samples. In addition, because bilirubin is often present bound to other proteins, e.g., serum albumin, the use of such surfactants in the spreading layer to achieve normalization of bilirubin transport advantageously appears to dissociate bilirubin bound to such protein. Preferred amounts of surfactant sufficient to achieve normalized bilirubin transport are typically between about 1% and about 15% by weight based on the dry weight of the layer. Further details regarding this use of surfactant materials to achieve normalized analyte transport can be found by reference to Goffe, Rand, and Wu, U.S. Pat. No. 4,050,898, issued Sept. 27, 1977.

Dry chemistry analytical elements useful in the present invention can be configured in a variety of forms, including elongated tapes of any desired width, sheets or smaller chips.

Preferred dry chemistry analytical elements are used by applying to the element a sample of liquid under analysis. Typically, an element will be formed such that an applied sample will contact a spreading layer prior to the reagent layer and will first contact such spreading layer at its surface furthest removed from such reagent layer.

After sample application, and desirably after the liquid sample has been taken up by a spreading layer, the element is exposed to any conditioning, such as heating, humidification, or the like, that is desirable to quicken or otherwise facilitate obtaining any test result. If an automated procedure is used, it is also desirable to have any spreading layer accomplish its function within several seconds.

After the analytical result is obtained as a detectable change, it is measured, usually by passing the element through a zone in which suitable apparatus for reflection or transmission spectrophotometry is provided. In one such apparatus a beam of energy, such as light, is directed through the support and the reagent layer. The light is then reflected, such as from an opacifying agent in the spreading and/or the radiation-blocking layer in the element, back to a detector or passes through the element to a detector, in the case of transmission detection.

Conventional calibration techniques are used to provide a control for the analysis. The standard solutions used in the calibration of the present $B_T$ assay can have a bilirubin content comprised of $B_u$, $B_c$, or a mixture of $B_u$ and $B_c$. The present $B_T$ assay advantageously provides accurate results regardless of the bilirubin composition used in the standard solutions.

The following Examples are presented to further illustrate the practice of the invention. The following materials were employed in the Examples:

Materials

Bilirubin standards: unconjugated bilirubin ($B_u$) was obtained from Sigma Chemical Company, St. Louis, Mo. Varying levels of $B_u$ were prepared in aqueous media (buffer solution or human serum pool) according to the method of Routh as described in Fundamentals of Clinical Chemistry, N. W. Tietz, Ed., 2nd Edition, W. B. Saunders Co., Philadelphia, Pa., (1964). Conjugated bilirubin ($B_c$) was obtained from human bile and prepared by a modified Lucassen procedure (Lucassen, J., "The Diazo Reaction of Bilirubin and Bilirubin Diglucuronide", Doctoral Thesis, University of Utrecht, The Netherlands, 1961) as described in the Wu et al paper presented at the American Association for Clinical Chemistry referenced in the Background of the Invention. The interactive mordants which were used are described hereinabove. All other chemicals were obtained from Eastman Organic Chemicals, Rochester, N.Y. Unless otherwise specified, all chemicals used in this study were reagent grade.

Human sera were supplied by local hospitals. Samples not immediately used were kept frozen at −25° C. and stored in the dark for no more than one week. Samples were not reused after thawing.

Multilayer analytical elements were prepared as described hereinabove and in a manner similar to that of Example 2 in U.S. Pat. No. 4,069,017 according to the following formats:

| | | g/m² |
|---|---|---|
| A. Multilayer Analytical Element Without Mordant | | |
| Reflecting-Spreading Layer | Blushed Cellulose Acetate | 7.0 |
| | $TiO_2$ | 50.0 |
| | Caffeine | 2.69 |
| | Sodium Benzoate | 4.035 |
| | Octylphenoxypolyethoxyethanol surfactant | 1.4 |
| Subbing Layer | Poly(N—isopropylacrylamide) | 0.387 |
| Reagent Layer | Deionized gelatin | 8.608 |
| | N,N—bis(2-hydroxyethyl)glycine (Bicine Buffer), 0.2 M, pH 8.0 | 3.5 |
| Support Layer | poly(ethylene terephthalate) | |
| B. Multilayer Analytical Element With Mordant | | |
| Reflecting-Spreading Layer | Blushed Cellulose Acetate | 7.0 |
| | $TiO_2$ | 50.0 |
| | Caffeine | 2.69 |
| | Sodium Benzoate | 4.035 |
| | Octylphenoxypolyethoxyethanol surfactant | 1.4 |
| Subbing Layer | Poly(N—isopropylacrylamide) | 0.387 |
| Reagent Layer | *Mordant 6 Table I | 1.72 |
| | Deionized gelatin | 8.608 |
| | N,N—bis(2-hydroxyethyl)glycine (Bicine Buffer) 0.2 M, pH 8.0 | 3.5 |
| Support Layer | poly(ethylene terephthalate) | |
| C. Multilayer Analytical Element With Mordant And Radiation-Blocking Layer | | |
| Reflecting-Spreading Layer | Blushed Cellulose Acetate | 7.0 |
| | $TiO_2$ | 50.0 |
| | Caffeine | 2.69 |
| | Sodium Benzoate | 4.035 |
| | Octylphenoxypolyethoxyethanol surfactant | 1.4 |
| Subbing Layer | Poly(N—isopropylacrylamide) | 0.387 |
| Radiation-Blocking Layer | Gelatin | 1.07 |
| | $TiO_2$ | 10.76 |
| Reagent Layer | Deionized gelatin | 8.608 |
| | Mordant 6 Table I | 1.72 |
| | N,N—bis(2-hydroxyethyl)glycine (Bicine Buffer) 0.2 M, pH 8.0 | 3.5 |
| Support Layer | poly(ethylene terephthalate) | |

*Mordant = poly(styrene-co-N—vinylbenzyl-N—benzyl-N,N—dimethyl ammonium chloride-co-divinyl benzene).

EXAMPLE 1

Determination of $B_T$ in Solution—Without Mordant

Bilirubin standards for $B_u$ and $B_c$ were gravimetrically prepared (and verified with nuclear magnetic resonance spectroscopy) using 0.05 M phosphate buffer, pH 7.0, to obtain final levels of 0.7 mg/dl and 1.4 mg/dl of each of $B_c$ and $B_u$. Phosphate buffer solutions served as the blank throughout. The solutions were placed in 1 cm cuvettes and scanned from 380 nm to 460 nm using a Cary Model 14 spectrophotometer (purchased from Varian Company, Instrument Division, Palo Alto, Calif., USA) at room temperature. FIGS. 1a–1i show the linear response curves (absorbance vs mg/dl) obtained at the various wavelengths. Because of the similarity of the linear response curves of $B_u$ and $B_c$ in the 400–420 nm region, these results demonstrated that the optimum wavelength to determine $B_T$ in solution (without an interactive mordant) was at ~400–420 nm, preferably 410 nm.

EXAMPLE 2

Determination of $B_T$ Using an Analytical Element—Without Mordant

Bilirubin standards were prepared as described in Example 1, except serum was used rather than phosphate buffer, to obtain final levels of $B_u$ of about 5.13, 9.73, 16.72, and 28.7 mg/dl and final levels of $B_c$ of about 1.0, 3.5, 7.1, and 14.2 mg/dl.

Ten microliters of each level of $B_u$ and $B_c$ were spotted onto elements prepared according to format A described above, and incubated for 5 minutes at 22° C. and about 50% relative humidity. (Similar results were achieved when testing was conducted at 37° C.) Water served as the blank throughout. Each analytical element was scanned from 380 to 490 nm, and the reflection density, $D_R$, was recorded on a spectrophotometer.

Figure 7B:
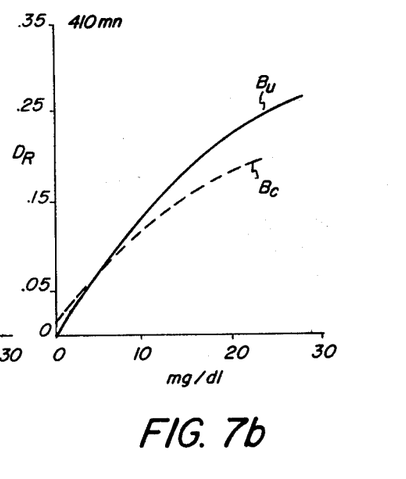

The response curves of $B_u$ and $B_c$ were most similar at a wavelength of about 385 nm, they were also effectively identical in the 400–410 nm region. The 400–410 nm region response curves exhibited greater assay sensitivity than did the 385 nm response curve. The response curves at 400 and 410 nm are shown in FIGS. 7a and 7b.

EXAMPLE 3

Determination of $B_T$ Using an Analytical Element—With Mordant

Figures 6B, 6C:
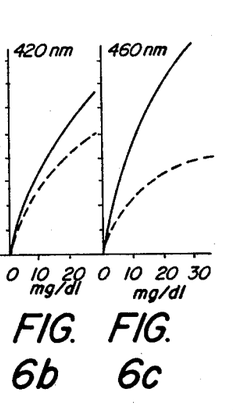

Test conditions were the same as described in Example 2, except that samples of $B_u$ and $B_c$ were spotted onto elements prepared according to Format B described above. The reflection densities were read at 400, 420, and 460 nm. As shown in FIGS. 6a–6c, the response curves of $B_u$ and $B_c$ were effectively identical in the 400–420 nm wavelength region, but quite different at 460 nm.

EXAMPLE 4

Effect of Varying Levels of Mordant Coverage in Analytical Elements

Analytical elements were prepared according to Format B except that the mordant coverage in each element varied 1X, 2X, 4X, i.e., 1.72 g/m², 3.44 g/m², 6.88 g/m². Bilirubin samples were spotted onto each element. Test conditions were identical to Example 2 above.

It was found that the reflection density response curves, regardless of mordant coverage, were most similar in the 400–420 nm wavelength regions.

EXAMPLE 5:

Effect of Additional Radiation-Blocking Layer in an Analytical Element

It was found that a radiation-blocking layer placed in the analytical element was effective in controlling potential interference from other serum components, e.g., hemoglobin, which absorb light in the same wavelength region as bilirubin. Three levels of $B_u$ (~0.9, 9.0, and 17 mg/dl) standards were prepared as described in Example 2, and each was spiked with two levels of human hemoglobin (50 and 200 mg/dl).

Ten microliters of each level of $B_u$/hemoglobin solution were spotted onto elements prepared according to Formats B and C described above, and incubated for 5 minutes at 37° C., after which the reflection density at 420 nm of each element was read and converted to mg/dl values using a Kodak EKTACHEM analyzer (Eastman Kodak Company, Rochester, N.Y., U.S.A.). Water served as the blank throughout.

Results summarized in Table II below show that the precision of the assay was improved using element C having the additional TiO$_2$ radiation-blocking layer. Element B gave an increasingly positive bias in the presence of hemoglobin.

TABLE II

| | Solutions Tested | | |
|---|---|---|---|
| Bilirubin mg/dl | Hemoglobin mg/dl | Element B (mg/dl) | Element C (Additional TiO$_2$ Blocking Layer) (mg/dl) |
| 0 | 0 | 0 | 0.0 |
| 0.9 | 0 | 0.85 | 0.85 |
| 0.9 | 50 | 1.30 | 1.00 |
| 0.9 | 200 | 2.40 | 1.10 |
| 9.0 | 0 | 8.60 | 8.40 |
| 9.0 | 50 | 9.55 | 8.50 |
| 9.0 | 200 | 10.65 | 8.20 |
| 17.0 | 0 | 17.05 | 16.05 |
| 17.0 | 50 | 17.65 | 16.05 |
| 17.0 | 200 | 18.55 | 16.70 |

EXAMPLE 6:

Correlation of Total Bilirubin Values Obtained Using an Analytical Element With a Reference Method Bilirubin standards were prepared as described in Example 2 to obtain final levels of $B_u$ of ~9.73 and 16.72 mg/dl and final levels of $B_c$ of ~7.1 and 14.2 mg/dl. Equal volumes of $B_u$ and $B_c$ standards were mixed to obtain two random mixtures of total bilirubin ($B_T$) as follows:

Solution I—9.73 mg/dl $B_u$ mixed with 7.1 mg/dl $B_c$ (1:1 v/v) to obtain 8.42 mg/dl $B_T$ (ratio $B_u/B_c \cong 0.7397$).

Solution II—16.72 mg/dl $B_u$ mixed with 14.2 mg/dl $B_c$ (1:1 v/v) to obtain 15.45 mg/dl $B_T$ (ratio $B_u/B_c \cong 0.85$).

Ten microliters of each level of $B_T$ were spotted onto an element prepared according to Format B described above, and incubated for 5 minutes at 22° C. and about 50% relative humidity. Water served as the blank throughout. The reflection density at 400 nm was recorded using a spectrophotometer and converted to mg/dl values. The results of the data, shown in Table III below, indicate excellent correlation between $B_T$ values as determined by a preferred method of the present invention (element with mordant) and the gravimetric reference method.

TABLE III

| Gravimetric Reference Method (mg/dl $B_T$) | Analytical Element With Mordant (Format B) (mg/dl $B_T$) |
|---|---|
| 8.42 | 8.89 |
| 15.45 | 15.30 |

EXAMPLE 7:

Correlation of the Method of the Present Invention with the Jendrassik-Grof Reference Method A random selection of serum samples (212) containing normal as well as abnormal levels of bilirubin ($B_T$) were obtained from a local hospital. Ten microliters of each sample were spotted onto elements prepared according to Format C described above, incubated for 5 minutes at 37° C., and the reflection density ($D_R$) of each element was recorded at 400 nm and converted to mg/dl values using a Kodak EKTACHEM analyzer. A serum blank was used throughout. Statistical analyses of the data, shown in Table IV, indicate excellent correlation between $B_T$ values as determined by a preferred method of the present invention (element with mordant) and the Jendrassik-Grof reference method. The Jendrassik-Grof reference method is described in Fundamentals of Clinical Chemistry, N. W. Tietz, Ed., 2nd Edition, W. B. Saunders Co., Philadelphia, PA, 1964, pp 1037–1040.

TABLE IV

| | Analytical Element with Mordant vs Jendrassik-Grof Reference Assay | *"Ideal Value" |
|---|---|---|
| Correlation Coefficient (r) | 0.991 | 1.0 |
| Slope of Regression Analysis | 0.929 | 1.0 |
| Intercept of Regression Analysis (Sy · x) | 0.46 | 0.0 |
| Number of Tests | 212 | |

*Ideal results are obtained when two tests correlate perfectly with no fixed or proportionate bias between them.

EXAMPLE 8:

Optimum Wavelength for Determining Total Bilirubin Using Concentration Units of mg/dl and Molarity The optimum wavelength at which $B_u$ and $B_c$ exhibit effectively identical absorption curves was found to be dependent upon the units chosen to express the concentration, i.e., units of mg/dl or units of molarity (M), as illustrated by the following test: Bilirubin standards were prepared as described in Example 2 to obtain the levels listed in Table V. The units of mg/dl were converted to equivalent units of molarity based on the molecular weights of $B_u$ and $B_c$. The molecular weight of $B_u$ is known to be 584, and that for $B_c$ was previously determined by the present inventor to be 918 as noted in the Background of The Invention.

Ten microliters of each level of $B_u$ and $B_c$ were spotted onto elements prepared according to Format C described above and incubated for 5 minutes at 22° C. and about 50% relative humidity. Water served as the blank throughout. The absorption spectrum was scanned from 360–600 nm on Perkin-Elmer 576 spectrophotometer, and the optimum wavelength for $B_T$ assay under these conditions was determined to be 395 nm. The reflection density, $D_R$, values obtained were converted to transmission density, $D_T$, values using the following empirically derived equation:

$$D_T = -0.194 + 0.469\, D_R + \frac{0.422}{1 + 1.179 e^{3.379\, D_R}}$$

FIGS. 2 and 3 show the data plotted as $D_R$ vs units of mg/dl and $D_T$ vs units of mg/dl, respectively, at 395 nm.

The optimum wavelength when using units of molarity under these conditions was determined to be 413 nm. FIGS. 4 and 5 show the data plotted with $D_R$ vs units of M and $D_T$ vs units of M, respectively, at 413 nm.

TABLE V

| mg/dl | Molarity |
|---|---|
| 0.53 | $0.09 \times 10^{-4}$ |
| 5.13 | $0.88 \times 10^{-4}$ |
| 9.73 | $1.66 \times 10^{-4}$ |
| 16.72 | $2.86 \times 10^{-4}$ |
| 23.70 | $3.92 \times 10^{-4}$ |
| 1.0 | $0.11 \times 10^{-4}$ |
| 3.5 | $0.38 \times 10^{-4}$ |
| 7.1 | $0.76 \times 10^{-4}$ |
| 14.2 | $1.53 \times 10^{-4}$ |
| 28.0 | $3.05 \times 10^{-4}$ |

The invention has been described in detail with particular reference to certain preferred embodiments thereof, but it will be understood that variations and modifications can be effected within the spirit and scope of the invention.

What is claimed is:

1. A spectrophotometric method for the determination of the $B_T$ content of an aqueous liquid, said method comprising:
   (a) contacting together said aqueous liquid and an essentially dry reagent zone of a test element, said reagent zone comprising an interactive mordant for bilirubin to mordant bilirubin, and
   (b) spectrophotometrically detecting in said test element the absorption spectrum of said aqueous liquid for $B_T$ at a wavelength within the range of from about 385 to about 425 nm at which the absorption characteristics of mordanted $B_u$ and mordanted $B_c$ are effectively identical.

2. A method as described in claim 1 wherein the absorption spectrum of said liquid is detected at a wavelength within the range of from about 395–420 nm.

3. A method as described in claim 1 wherein said interactive mordant represents a polymeric mordant having repeating units of the formula:

wherein
   A represents an organo group constituting a portion of the polymer backbone;
   Q represents a chemical bond(s) or a chemical group linking $M^\oplus$ to A;
   $M^\oplus$ represents a hydrophobic organic moiety containing a cation, and
   $X^\ominus$ represents an acid anion.

4. A method as described in claim 1 wherein said interactive mordant represents a copolymer having up to about 90 wt% of non-interfering hydrophobic repeating units and 10 to 90 wt% of repeating units having the formula:

wherein
   A represents an organo group constituting a portion of the polymer backbone;
   Q represents a chemical bond(s) or a chemical group linking $M^\oplus$ to A;
   $M^\oplus$ represents a hydrophobic organic moiety containing a quaternary ammonium group;
   $X^\ominus$ represents an acid anion.

5. A method as described in claim 1 wherein said interactive mordant represents a copolymer having up to about 90 wt% of non-interfering hydrophobic repeating units and 10 to 90 wt% of repeating units having the formula:

wherein
   A represents an organo group constituting a portion of the polymer backbone;
   Q represents a chemical bond(s) or a chemical group linking $M^\oplus$ to A;
   $M^\oplus$ has the formula:

wherein
   each of $R^1$, $R^2$ and $R^3$, which are the same or different, represent an alkyl, an aryl, an aralkyl, or an alkaryl group.

6. A method as described in claim 1 wherein said liquid is serum.

7. A method as described in claim 1 wherein said step (a) is carried out by contacting together said aqueous liquid and said interactive mordant in a noninterfering liquid medium.

8. A method as described in claim 1 wherein said step (a) is carried out at a pH of from about 6.5 to 10.0 and a temperature within the range of from about 15° to 60° C.

9. A method as described in claim 1 wherein said mordant is a member selected from the group consisting of poly(N,N,N-trimethyl-N-vinylbenzylammonium chloride), poly[styrene-co-benzyl(dimethyl)-p-vinylbenzylammonium chloride], poly(N,N,N-trioctyl-N-vinylbenzylphosphonium chloride), poly[styrene-co-(vinylbenzyl)-(trihexyl)-ammonium chloride], poly(N,N,N-trimethyl-N-vinylbenzylammonium chloride-co-styrene) and poly(styrene-co-N-vinylbenzyl-N-benzyl-N,N-dimethylammonium chloride-codivinylbenzene).

10. A method as described in claim 1 wherein said reagent zone represents a reagent layer of a multilayer analytical test element comprising a reflecting spreading layer and said reagent layer as superposed layers on a radiation-transmissive support.

11. A method as described in claim 1 wherein said analytical element also contains a bilirubin promoter.

12. A method as described in claim 1 wherein said analytical element also contains caffeine, sodium benzoate, or a mixture thereof.

13. A method as described in claim 1 wherein said reagent zone represents a reagent layer of a multilayer analytical test element comprising a reflecting spreading layer, a radiation-blocking layer, and said reagent layer as superposed layers on a radiation-transmissive support.

14. A method as described in claim 13, wherein said radiation-blocking layer contains titanium dioxide.

* * * * *